(12) United States Patent
Liu et al.

(10) Patent No.: US 7,399,280 B2
(45) Date of Patent: Jul. 15, 2008

(54) PASSIVE AND WIRELESS IN-VIVO ACOUSTIC WAVE FLOW SENSOR

(75) Inventors: James Z. Liu, Rockford, IL (US); Richard A. Alderman, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 579 days.

(21) Appl. No.: 10/829,729

(22) Filed: Apr. 21, 2004

(65) Prior Publication Data

US 2005/0240110 A1     Oct. 27, 2005

(51) Int. Cl.
*A61B 5/04* (2006.01)
*H01L 41/00* (2006.01)
*H02N 2/00* (2006.01)

(52) U.S. Cl. ............... 600/504; 310/313 R; 310/313 B; 73/861.18; 73/204.23

(58) Field of Classification Search ......... 600/500–507, 600/300, 301; 73/861, 861.18, 204.23, 24.03; 310/313 R, 313 B
See application file for complete search history.

(56) References Cited

U.S. PATENT DOCUMENTS

| | | | |
|---|---|---|---|
| 4,726,225 A * | 2/1988 | Brace et al. ............. 73/204.23 |
| 4,932,255 A * | 6/1990 | Brace et al. ............. 73/204.11 |
| 5,003,822 A | 4/1991 | Joshi |
| 5,155,708 A | 10/1992 | Bedi et al. ................. 367/152 |
| 5,821,425 A | 10/1998 | Mariani et al. ............. 73/703 |
| 5,967,986 A | 10/1999 | Cimochowski et al. |
| 6,092,530 A * | 7/2000 | Weissman et al. ............ 128/899 |
| 6,170,318 B1 | 1/2001 | Lewis ........................ 73/23.34 |
| 6,206,835 B1 * | 3/2001 | Spillman et al. ............ 600/485 |
| 6,293,136 B1 | 9/2001 | Kim .......................... 73/19.03 |
| 6,314,791 B1 | 11/2001 | Rapp et al. ................. 73/24.06 |
| 6,330,885 B1 * | 12/2001 | Weissman et al. ........... 128/899 |
| 6,331,244 B1 | 12/2001 | Lewis et al. ............... 205/777.5 |
| 6,568,271 B2 | 5/2003 | Shah et al. ..................... 73/599 |
| 6,640,613 B2 | 11/2003 | Rapp et al. ................. 73/24.01 |

(Continued)

FOREIGN PATENT DOCUMENTS

EP          0261393          3/1988

OTHER PUBLICATIONS

Johannes Nieβ, et al., "A miniaturized thermal desorption unit for chemical sensing below odor threshold", Sensor and Actuators, B 95 (2003), pp. 1-5.
John R. Vig, "Dual-mode Oscillators for Clocks and Sensors", 1999 IEEE Ultrasonics Symposium, pp. 859-868.
James Z. Liu, "Construction Optimization for Acoustic Wave Chemical Sensor Selectivity", (all pages), Sensor Expo Detroit, Sep. 2000.

(Continued)

*Primary Examiner*—Charles A. Marmor, II
*Assistant Examiner*—Navin Natnithithadha
(74) *Attorney, Agent, or Firm*—Kermit D. Lopez; Luis M. Ortiz; William B. Shelby

(57) ABSTRACT

A wireless surface wave flow sensor can be utilized for monitoring the flow of fluid. Such a surface wave flow sensor can be configured to include one or more interdigital transducers and a self-heating heater formed upon a piezoelectric substrate. The interdigital transducer(s) can be selected to convert electrical signals to surface waves thereof. An antenna can also be connected to the surface wave device, wherein the antenna can receive one or more signals, which excites the acoustic device to produce a frequency output associated with the flow of the fluid for analysis thereof.

20 Claims, 4 Drawing Sheets

U.S. PATENT DOCUMENTS

| | | | |
|---|---|---|---|
| 6,710,515 B2 | 3/2004 | Lu et al. | 310/313 |
| 2002/0113521 A1 | 8/2002 | Rapp et al. | 310/313 R |
| 2003/0076743 A1 | 4/2003 | Thompson et al. | 367/140 |
| 2003/0196477 A1 | 10/2003 | Auner et al. | 73/24.06 |

OTHER PUBLICATIONS

PCT-Notification of Transmittal of The International Search Report and the Written Opinion of the International Searching Authority, or the Declaration, Date of Mailing Jul. 9, 2005.

* cited by examiner

US 7,399,280 B2

PASSIVE AND WIRELESS IN-VIVO ACOUSTIC WAVE FLOW SENSOR

TECHNICAL FIELD

Embodiments are generally related to flow sensing devices and techniques. Embodiments are also related to interdigital surface wave sensor devices, such as, for example, surface acoustic wave (SAW), shear-horizontal surface acoustic wave (SH-SAW), pseudo (or leaky) SH-SAW, love wave, and shear-horizontal acoustic plate mode (SH-APM) devices and sensors.

BACKGROUND OF THE INVENTION

Surface wave sensors can be utilized in a number of sensing applications. Examples of surface wave sensors include devices such as acoustic wave sensors, which can be utilized to detect the presence of substances, such as chemicals. An acoustic wave (e.g., SAW/SH-SAW/Love/SH-APM) device acting as a sensor can provide a highly sensitive detection mechanism due to the high sensitivity to surface loading and the low noise, which results from their intrinsic high Q factor.

Surface acoustic wave devices are typically fabricated using photolithographic techniques with comb-like interdigital transducers placed on a piezoelectric material. Surface acoustic wave devices may have either a delay line or a resonator configuration. The change of the acoustic property due to the flow can be interpreted as a delay time shift for the delay line surface acoustic wave device or a frequency shift for the resonator (SH-SAW/SAW) acoustic wave device.

Acoustic wave sensing devices often rely on the use of piezoelectric crystal resonator components, such as the type adapted for use with electronic oscillators. In a typical flow sensing application, the heat convection can change the substrate temperature, while changing the SAW device resonant frequency. With negative temperature coefficient materials such as $LiNbO_3$, the oscillator frequency is expected to increase with increased liquid flow rate. The principle of sensing is similar to classical anemometers.

Flow rate is an important parameter for many applications. The monitoring of liquid (e.g., blood, saline, etc.) flow rate within a human body can provide important information for medical research and clinical diagnosis. Such measurements can provide researchers with insights into, for example, the physiology and functioning of the heart and other human organs, thereby leading to advances in medical, nutrition and related biological arts. Blood/liquid flow rate measurements can also provide useful information regarding the safety and efficacy of pharmaceuticals and the toxicity of chemicals. It is believed that the use of passive, wireless acoustic wave devices for flow rate monitoring can provide for great advances in physiological, pharmaceutical and medical applications to name a few. Surface acoustic wave sensors have the potential to provide flow sensor systems with higher sensitivity and wider dynamic ranges than the solid state flow sensor devices currently available.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide improved flow sensor devices and sensing techniques.

It is another aspect of the present invention to provide for an improved surface wave flow sensor device.

It is yet a further aspect of the present invention to provide for an interdigital surface wave device, such as, for example, surface acoustic wave (SAW) resonator or surface acoustic wave (SAW) delay line sensing devices, which can be adapted for use in flow sensing applications.

The aforementioned aspects of the invention and other objectives and advantages can now be achieved as described herein. Fluid flow sensing systems and methods are disclosed. A surface wave flow sensor can be utilized for monitoring the flow of fluid. Such a surface wave flow sensor can be configured, according to one embodiment, to include one or more interdigital transducers and a heater formed upon a piezoelectric substrate. The interdigital transducer can be selected to convert electrical signals to surface waves thereof.

An antenna can also be connected to the surface wave device, wherein the antenna is for receiving one or more signals, which excites the acoustic wave device (i.e., resonator and delay line) to produce a frequency output associated with the flow of the fluid for analysis thereof. Additionally, one or more other transmitter/receivers can also be utilized for transmitting signals to the antenna for exciting the interdigital transducer to produce one or more frequency outputs associated with the flow of the fluid for analysis thereof. The fluid itself can be human blood and the surface wave flow sensor and the antenna can be implantable within a human body for monitoring the blood.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment of the present invention and are not intended to limit the scope of the invention.

Figure 1:
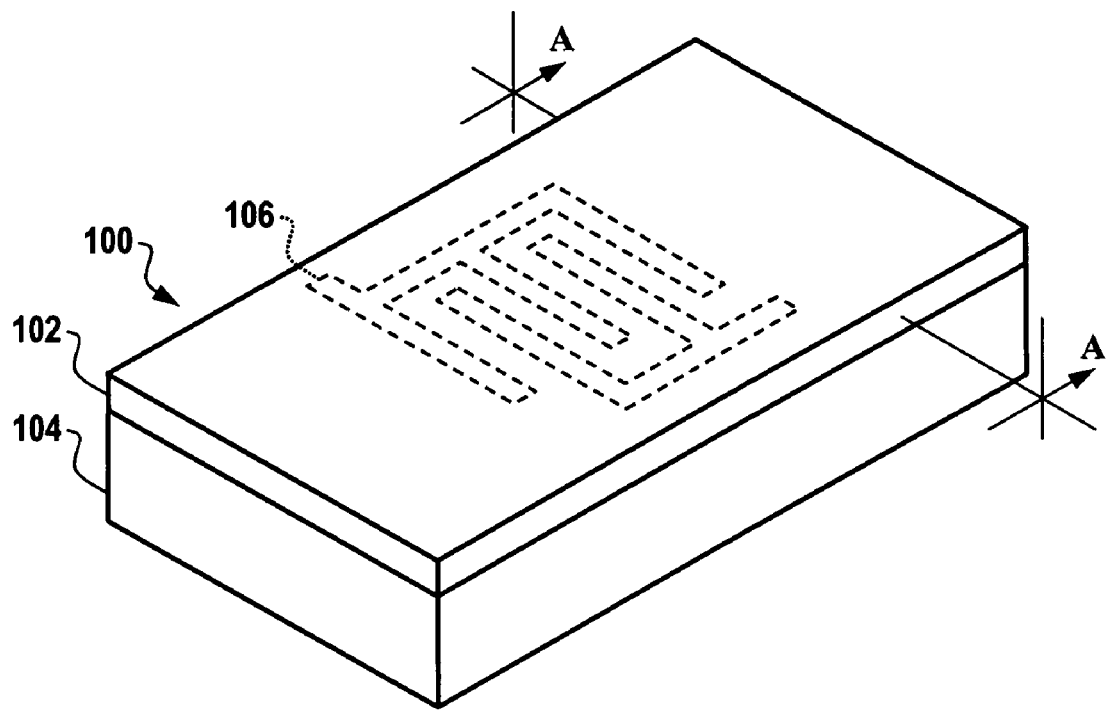
FIG. 1 illustrates a perspective view of an interdigital surface wave device, which can be adapted for use with one embodiment of the present invention.

FIG. 1 illustrates a perspective view of an interdigital surface wave device 100, which can be implemented in accordance with one embodiment of the present invention. Surface wave device 100 can be adapted for use in fluid flow sensing activities, as described in further detail herein. Surface wave device 100 can be configured to generally include an interdigital transducer 106 formed on a piezoelectric substrate 104. The surface wave device 100 can be implemented in the context of a sensor chip. Interdigital transducer 106 can be configured in the form of an electrode.

Figure 2:
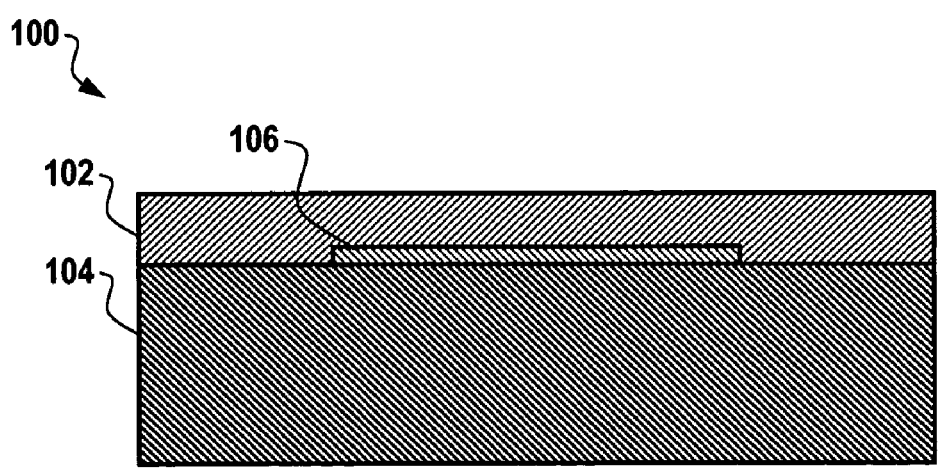
FIG. 2 illustrates a cross-sectional view along line A-A of the interdigital surface wave device depicted in FIG. 1, which can be adapted for use with one embodiment of the present invention.

FIG. 2 illustrates a cross-sectional view along line A-A of the interdigital surface wave device 100 depicted in FIG. 1, in accordance with one embodiment of the present invention. Piezoelectric substrate 104 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few. Interdigital transducer 106 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAI. Third, interdigital transducer 106 can be formed from metal-nonmetal compounds (e.g., ceramic electrodes based on TiN, $COSi_2$, or WC). Depending on the biocompatibility of the substrate and interdigital transducer materials, a thin layer of biocompatible coating 102 may be used to cover the interdigital transducer and the substrate.

Figure 3:
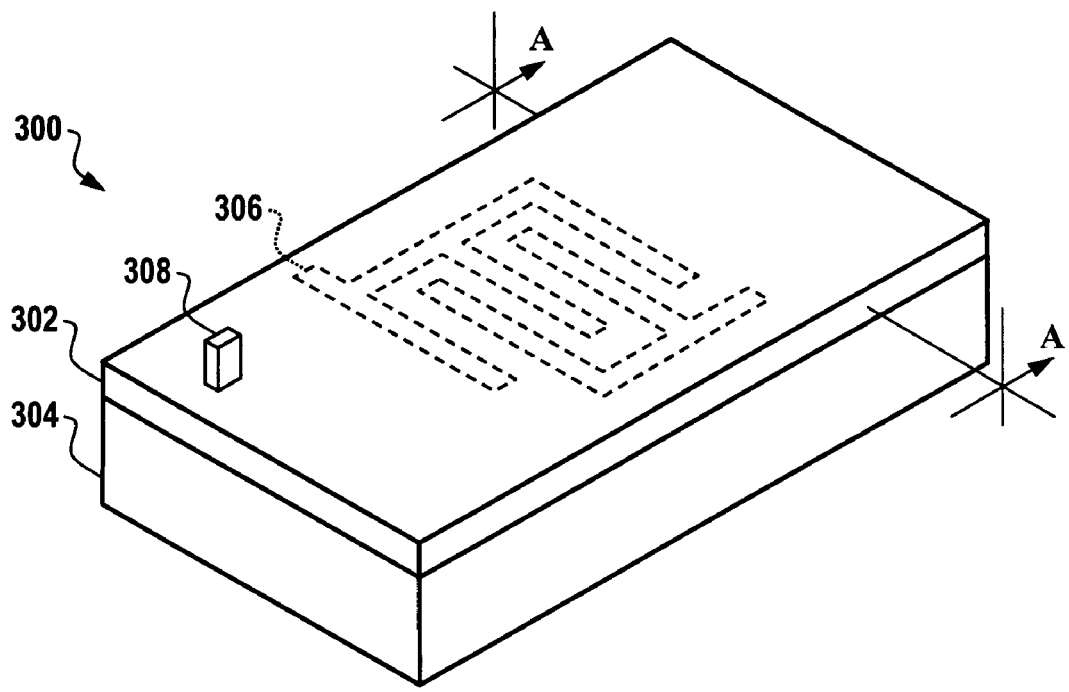
FIG. 3 illustrates a perspective view of an interdigital surface wave device, which can be adapted for use with one embodiment of the present invention.
Figure 4:
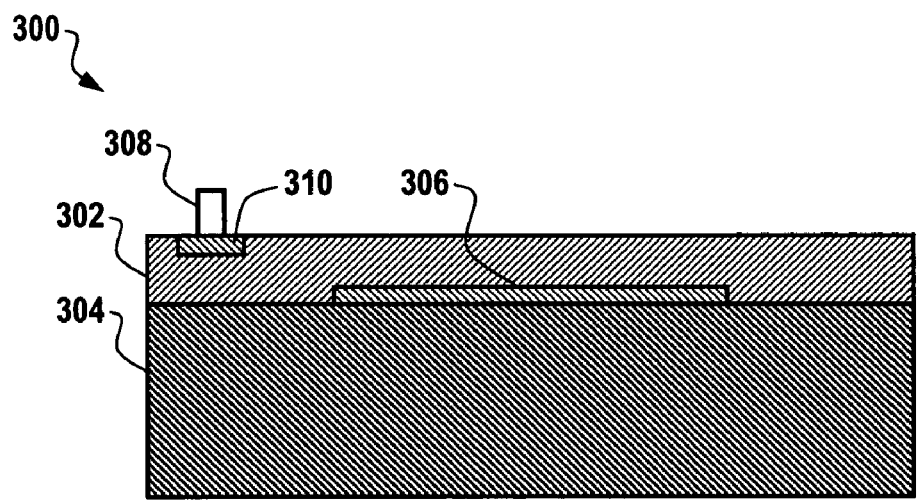
FIG. 4 illustrates a cross-sectional view along line A-A of the interdigital surface wave device depicted in FIG. 3, which can be adapted for use with one embodiment of the present invention.

FIG. 3 illustrates a perspective view of an interdigital surface wave device 300, which can be implemented in accordance with an alternative embodiment of the present invention. The configuration depicted in FIGS. 3-4 is similar to that illustrated in FIGS. 1-2, with the addition of an antenna 308, which is connected to and disposed above a wireless excitation component 310 (i.e., shown in FIG. 4). Surface wave device 300 generally includes an interdigital transducer 306 formed on a piezoelectric substrate 304. Surface wave device 300 can therefore function as an interdigital surface wave device, and one, in particular, which utilizing surface-skimming bulk wave techniques. Interdigital transducer 306 can be configured in the form of an electrode. A biocompatible coating 302 can be selected such that there will be no adverse effect to the human body. Various selective coatings can be utilized to implement coating 302.

A change in acoustic properties can be detected and utilized to identify or detect the substance or species absorbed and/or adsorbed by the interdigital transducer 306. Thus, interdigital transducer 306 can be excited via wireless means to implement a surface acoustical model. Thus, antenna 308 and wireless excitation component 310 can be utilized to excite one or more frequency modes associated with the flow of a fluid for fluid flow analysis thereof.

FIG. 4 illustrates a cross-sectional view along line A-A of the interdigital surface wave device 300 depicted in FIG. 3, in accordance with one embodiment of the present invention. Thus, antenna 308 is shown in FIG. 4 disposed above coating 302 and connected to wireless excitation component 310, which can be formed within an area of coating 302. Similar to the configuration of FIG. 2, Piezoelectric substrate 304 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few.

Interdigital transducer 306 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAI. Third, interdigital transducer 306 can be formed from metal-nonmetal compounds (e.g., ceramic electrodes based on TiN, $CoSi_2$, or WC).

Figure 5:
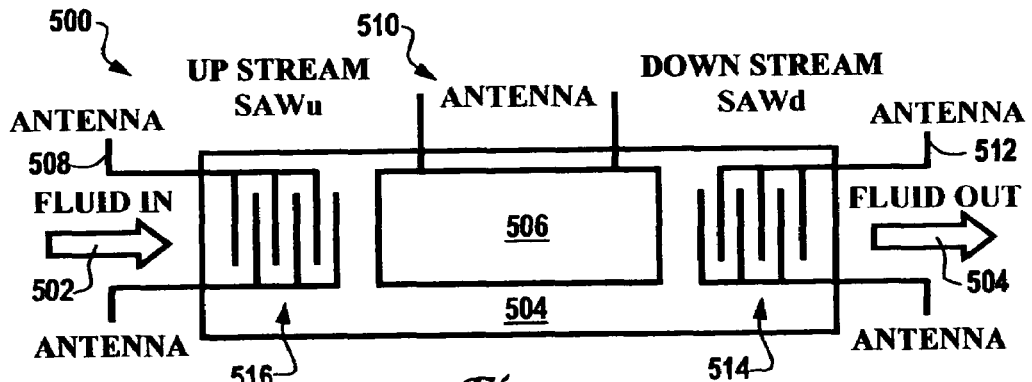
FIG. 5 illustrates a block diagram of a wireless surface acoustic wave flow sensor system, which can be implemented in accordance with a preferred embodiment of the present invention.

FIG. 5 illustrates a block diagram depicted a perspective view of a wireless SAW flow sensor system 500, which can be implemented in accordance with a preferred embodiment of the present invention. System 500 includes a compartment or structure 504 in which a self-heating heater 506 and an upstream SAWu sensor device 516 can be located. Structure 504 additionally can include a down stream SAWd sensor device 514. Sensor devices 516 and 514 can be implemented as interdigital transducers similar to those depicted in FIGS. 1-4.

Arrows 502 and 504 respectively indicate fluid flow in and fluid out from compartment or structure 504. An antenna 508 can be integrated with and/or connected to up stream SAWu sensor device 516. Similarly, a second antenna 512 can be integrated with and/or connected to SAWd down stream sensor device 514. Additionally, a third antenna 510 can be integrated with and/or connected to self-heating heater 506. Note that self-heating heater 506 can be powered by converting RF power to heat.

The self-heating heater 506 can absorbs energy from RF power and convert it to heat. This self-heating portion can be formed from acoustically "lossy" materials, or acoustical absorber, in which the dissipation of acoustic energy in such material causes heating of the substrate. For a given thermal conductivity and effective thermal mass of the substrate, the quiescent surface temperature can eventually achieve steady state. Self-heating heater 506 can also be configured from a resistor-heater type material.

Figure 6:
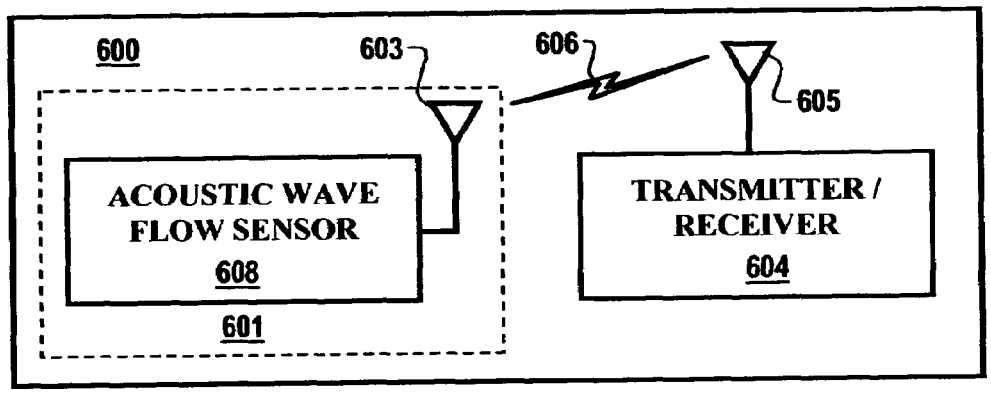
FIG. 6 illustrates a block diagram of an in-vivo acoustic wave flow sensor system, which can be implemented in accordance with a preferred embodiment of the present invention.

FIG. 6 illustrates a block diagram of an in-vivo acoustic wave flow sensor system 600, which can be implemented in accordance with a preferred embodiment of the present invention. System 600 generally includes an acoustic wave flow sensor device 608, which can be implemented in a configuration similar to that of sensor system 500 depicted in FIG. 5. For example, acoustic wave flow sensor device 608 can be equipped with one or more digital transducers, such as those depicted in FIG. 5.

Device 608 can be configured to include an acoustic coating such as that depicted in FIG. 1. Acoustic wave flow sensor device 608 can be coupled to and/or integrated with an antenna 603. Antenna 603 can receive and/or transmit data to and from a transmitter/receiver 604. In general, the antenna 603 can be connected to device 608, such that antenna 605 receives one or more signals, which can excite an acoustic device thereof to produce a frequency output associated with the flow of fluid for analysis thereof.

Acoustic wave flow sensor device 608 and antenna 603 together can form a passive, wireless, in vivo acoustic wave flow sensor device 601, which can be implanted within a human being. Wireless interrogation, as represented by arrow 606 can provide the power and data collection necessary for the proper functioning of device 601. Device 601 can be implemented via a variety of surface acoustic wave technologies, such as Rayleigh waves, shear horizontal waves, love waves, and so forth.

Figure 7:
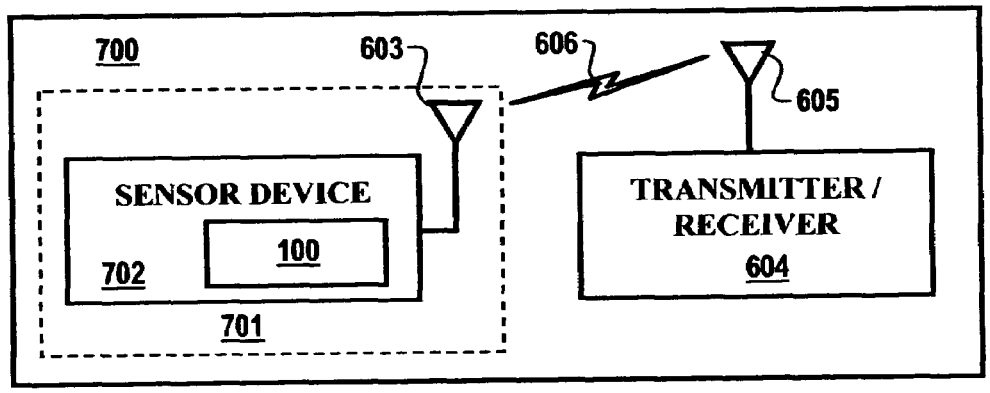
FIG. 7 illustrates a block diagram of an in-vivo acoustic wave flow sensor system 700, which can be implemented in accordance with an alternative embodiment of the present invention.

FIG. 7 illustrates a block diagram of an in-vivo acoustic wave flow sensor system 700, which can be implemented in accordance with an alternative embodiment of the present invention. Note that in FIGS. 6 and 7, identical parts or elements are generally indicated by identical reference numerals. System 700 is therefore similar to system 600 depicted in FIG. 6, but includes some slight modifications. For example, a sensor device 702 is utilized in place of device 520. Sensor device 702 incorporates device 100 depicted in FIG. 1. Thus, sensor device 702 and transmitter/receiver 602 together form a sensing device 701, which can be utilized to monitor liquid flow rate, such as, for example, that of human blood flowing within a human body.

Figure 8:
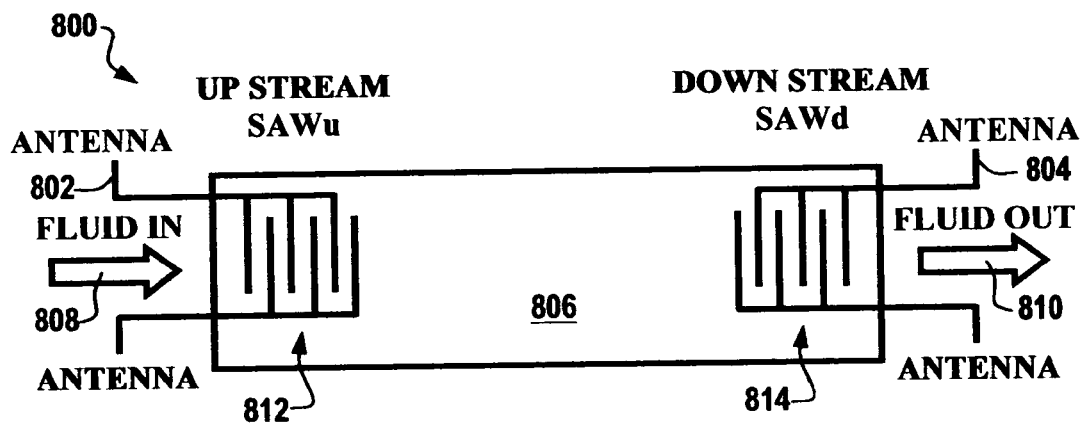
FIG. 8 illustrates a block diagram of a wireless surface acoustic wave flow sensor system without a heater, which can be implemented in accordance with an alternative embodiment of the present invention.

FIG. 8 illustrates a block diagram of a wireless surface acoustic wave flow sensor system 800, which can be implemented without a heater, in accordance with an alternative embodiment of the present invention. System 800 generally includes a compartment or structure 806 in which an upstream SAWu sensor device 812 can be located. Structure 806 additionally can include a down stream SAWd sensor device 814. Sensor devices 812 and 814 can be implemented, for example, as interdigital transducers similar to those depicted in FIGS. 1-4.

Arrows 808 and 810 respectively indicate fluid flow in and fluid out of compartment or structure 806. An antenna 802 can be integrated with and/or connected to up stream SAWu sensor device 812. Similarly, a second antenna 814 can be integrated with and/or connected to SAWd down stream sensor device 814.

Figure 9:
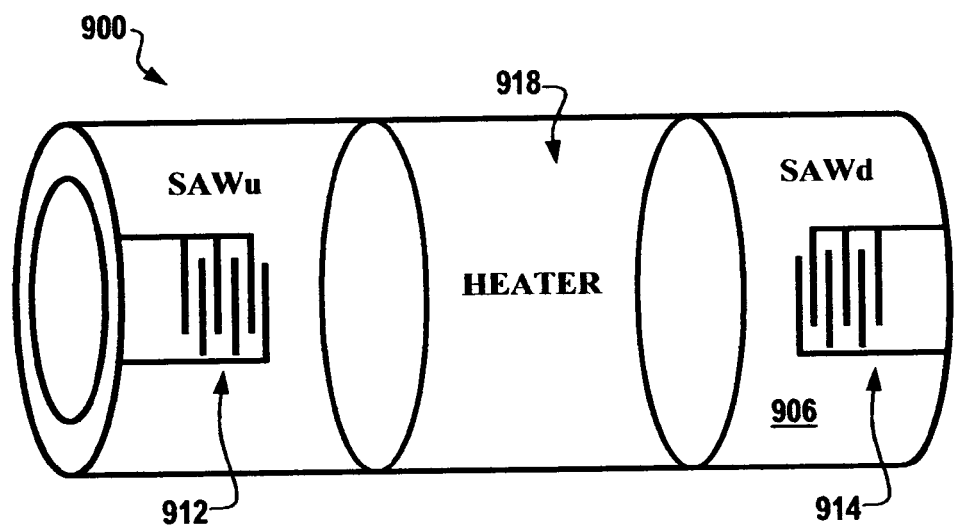
FIG. 9 illustrates a block diagram of a cylindrical shape wireless surface acoustic wave flow sensor system, which can be implemented in accordance with an alternative embodiment of the present invention.

FIG. 9 illustrates a block diagram of a cylindrical shape wireless surface acoustic wave flow sensor system 900, which can be implemented in accordance with an alternative embodiment of the present invention. System 900 includes a cylindrical-shaped compartment or structure 906 in which a self-heating heater 918 and an upstream SAWu sensor device 912 can be located. Structure 906 additionally can include a down stream SAWd sensor device 914. Sensor devices 912 and 914 can be, for example, implemented as interdigital transducers similar to those depicted in FIGS. 1-4. The SAWu sensor device 912, heater 918 and SAWd sensor device 914 can be located on the inside wall of structure 906 with respective connections at the ends thereof. In the configuration of system 900, 350 degrees of the inside circumference can be utilized for the heater resistor or heater 918, which leaves sufficient space for configuring all connects at the edges of structure 906.

In terms of coating selection, biocompatibility involves the acceptance of an artificial implant by the surrounding tissue and by the body as a whole. Biocompatible materials do not irritate the surrounding structures, do not provoke an abnormal inflammatory response, do not incite allergic reactions, and do not cause cancer.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The invention claimed is:

1. A fluid flow sensing system, comprising:
   a piezoelectric substrate;
   a surface acoustic wave flow sensor for monitoring a flow of fluid through a cylindrically-shaped compartment formed from a plurality of walls, said surface acoustic wave flow sensor comprising at least one upstream surface acoustic wave sensing device and at least one downstream surface acoustic wave sensing device, said surface acoustic wave flow sensor comprising at least one interdigital transducer and a self-heating heater formed upon said piezoelectric substrate wherein said self-heating heater is disposed between said at least one upstream surface acoustic wave sensing device and said at least one downstream surface acoustic wave sensing device, said interdigital transducer comprising an electrode material that is selected to convert negligible electrical coupling to surface waves thereof;
   a first antenna connected to said self-heating heater to receive RF energy wherein said self-heating heater absorbs said RF energy and converts said RF energy to heat; and
   a second antenna integrated with said at least one interdigital transducer, wherein said second antenna receives at least one signal, which excites said at least one interdigital transducer to produce a frequency output associated with said flow of said fluid for analysis thereof.

2. The system of claim 1 further comprising a transmitter and receiver unit for transmitting said at least one signal to said second antenna for exciting said at least one interdigital transducer to produce said at least one frequency output associated with said flow of said fluid for analysis thereof.

3. The system of claim 2 wherein said fluid comprises blood and wherein said surface acoustic wave flow sensor and said second antenna thereof are implantable within a human body for monitoring said blood and wherein said transmitter and receiver unit is located outside of said human body.

4. The system of claim 1 wherein said at least one interdigital transducer comprises electrode materials selected from among a group of materials comprising at least one of the following metals: Al, Pt, Au, Rh, Ir, Cu, Ti, W, Cr, or Ni.

5. The system of claim 1 wherein said at least one interdigital transducer comprises electrode materials selected from among a group of materials comprising alloys.

6. The system of claim 1 wherein said at least one interdigital transducer comprises electrode materials selected from among a group of materials comprising metal-nonmetal compounds.

7. A fluid flow sensing system, comprising:
   a piezoelectric substrate;
   a surface acoustic wave flow sensor for monitoring a flow of fluid for monitoring a flow of fluid through a cylindrically-shaped compartment formed from a plurality of walls including an inside wall thereof, wherein said surface acoustic wave flow sensor comprises at least one interdigital transducer and a self-heating heater formed upon said piezoelectric substrate wherein said self-heating heater is disposed between said at least one upstream surface acoustic wave sensing device and said at least one downstream surface acoustic wave sensing device, wherein said at least one interdigital transducer comprises an electrode material that is selected to convert negligible electrical coupling to surface waves thereof, said at least one interdigital transducer constituting at least one upstream surface acoustic wave device and at least one downstream surface acoustic wave device, wherein said at least one upstream surface acoustic wave device, said at least one downstream surface acoustic wave device and said self-heating heater are located on said inside wall of said structure;

a first antenna connected to said self-heating heater to receive RF energy wherein said self-heating heater absorbs said RF energy and converts said RF energy to heat;

a second antenna integrated with said at least one interdigital transducer, wherein said second antenna receives at least one signal, which excites said at least one interdigital transducer to produce a frequency output associated with said flow of said fluid for analysis thereof, wherein said fluid comprises blood and wherein said surface acoustic wave flow sensor and said second antenna are implantable within a human body for monitoring said blood; and a transmitter and receiver unit for transmitting said at least one signal to said second antenna for exciting said at least one interdigital transducer to produce said at least one frequency output associated with said flow of said fluid for analysis thereof, wherein said transmitter and receiver unit is located outside of said human body.

8. The system of claim 7 wherein said at least one interdigital transducer comprise electrode materials selected from among a group of materials comprising at least one of the following metals: Al, Pt, Au, Rh, Ir, Cu, Ti, W, Cr, or Ni.

9. The system of claim 7 wherein said at least one interdigital transducer comprises electrode materials selected from among a group of materials comprising alloys.

10. The system of claim 7 wherein said at least one interdigital transducer comprises electrode materials selected from among a group of materials comprising metal-nonmetal compounds.

11. The system of claim 7 wherein said cylindrically-shaped structure comprises an inside circumference wherein 350 degrees of said inside circumference are utilized in forming said self-heating heater in order to provide a sufficient space for configuring all connections thereof at least one edge of said cylindrically shaped structure.

12. A fluid flow sensing method, comprising the steps of:
providing a piezoelectric substrate;
configuring upon said piezoelectric substrate, a surface acoustic wave flow sensor for monitoring a flow of fluid;
configuring said surface wave flow sensor to comprise at least one interdigital transducer and a biocompatible acoustic coating formed upon said piezoelectric substrate, said at least one interdigital transducer comprising at least one upstream surface acoustic wave sensing device and at least one downstream surface acoustic wave sensing device, wherein said at least one interdigital transducer comprises an electrode material that is selected to convert negligible electrical coupling to surface waves thereof and a self-heating heater formed upon said piezoelectric substrate wherein said self-heating heater is disposed between said at least one upstream surface acoustic wave sensing device and said at least one downstream surface acoustic wave sensing device;

connecting a first antenna to said self-heating heater to receive RF energy wherein said self-heating heater absorbs said RF energy and converts said RF energy to heat; and integrating a second antenna to surface acoustic wave device, wherein said second antenna receives at least one signal, which excites said at least one interdigital transducer to produce a frequency output associated with said flow of said fluid for analysis thereof.

13. The method of claim 12 further comprising the step of providing a transmitter and receiver unit for transmitting said at least one signal to said second antenna for exciting said at least one interdigital transducer to produce said at least one frequency output associated with said flow of said fluid for analysis thereof.

14. The method of claim 12 wherein said fluid comprises blood and wherein said surface wave flow sensor and said second antenna are implantable within a human body for monitoring said blood.

15. The method of claim 12 wherein said at least one interdigital transducer comprise electrode materials selected from among a group of materials comprising at least one of the following metals: Al, Pt, Au, Rh, Ir, Cu, Ti, W, Cr, or Ni.

16. The method of claim 12 wherein said at least one interdigital transducer comprises electrode materials selected from among a group of materials comprising alloys.

17. The method of claim 16 further comprising:
providing a transmitter and receiver unit for transmitting said at least one signal to said second antenna for exciting said at least one interdigital transducer to produce said at least one frequency output associated with said flow of said fluid for analysis thereof, wherein said fluid comprises blood and wherein said surface wave flow sensor and said second antenna are implantable within a human body for monitoring said blood.

18. The method of claim 12 wherein said at least one interdigital transducer comprises electrode materials selected from among a group of materials comprising metal-nonmetal compounds.

19. The method of claim 18 further comprising:
providing a transmitter and receiver unit for transmitting said at least one signal to said second antenna for exciting said at least one interdigital transducer to produce said at least one frequency output associated with said flow of said fluid for analysis thereof, wherein said fluid comprises blood and wherein said surface wave flow sensor and said second antenna are implantable within a human body for monitoring said blood.

20. The method of claim 12 further comprising:
providing a transmitter and receiver unit for transmitting said at least one signal to said second antenna for exciting said at least one interdigital transducer to produce said at least one frequency output associated with said flow of said fluid for analysis thereof, wherein said fluid comprises blood and wherein said surface wave flow sensor and said second antenna are implantable within a human body for monitoring said blood.

* * * * *